United States Patent [19]

Sänger

[11] Patent Number: 4,777,907

[45] Date of Patent: Oct. 18, 1988

[54] APPARATUS FOR FEEDING TEST STRIPS AUTOMATICALLY INTO AN ANALYZER

[75] Inventor: Hans D. Sänger, Frankfurt am Main, Fed. Rep. of Germany

[73] Assignee: Hoechst Aktiengesellschaft, Fed. Rep. of Germany

[21] Appl. No.: 78,708

[22] Filed: Jul. 28, 1987

[30] Foreign Application Priority Data

Jul. 30, 1986 [DE] Fed. Rep. of Germany ....... 3625705

[51] Int. Cl.$^4$ .................. B05B 15/04; B05B 12/00
[52] U.S. Cl. .................................. 118/687; 118/679; 118/323; 198/533; 198/399; 198/400
[58] Field of Search ............... 118/323, 676, 677, 679, 118/686, 687; 422/66, 68; 198/533, 397, 399, 400, 463.6

[56] References Cited

U.S. PATENT DOCUMENTS

| | | | |
|---|---|---|---|
| 3,070,064 | 12/1962 | Busse | 118/687 |
| 3,385,261 | 5/1968 | Wittemann et al. | 118/323 X |
| 3,841,858 | 10/1974 | Akashi et al. | 118/323 X |
| 4,469,723 | 9/1984 | Haq | 118/686 |

*Primary Examiner*—Shrive P. Beck
*Attorney, Agent, or Firm*—Finnegan, Henderson, Farabow, Garrett & Dunner

[57] ABSTRACT

In the apparatus for feeding test strips automatically into an analyzer, in order to separate these, fix the position of the test zones and reverse the test strips and moisten their test zones with liquid, a supply container (1) for the test strips (13) is equipped with an orifice (14), in which a transport device (12) is arranged. The transport device is equipped with a guide plate (7) and with drivers and has noses (19, 19a) which interact with a moveably arranged bar (11) projecting into the orifice (14). The guide plate (7) merges into a guide (8) which opens into a reversing device (2, 2a). Between guide (8) and reversing device is arranged a closing means (9) for the guide (8), the said closing means being connected via a lever (5) to a holding device (10) for the test strips (13), and the holding device projects into the guide and is mounted rotatably in synchronism with the closing means. It is also equipped with a drive device (16). The reversing device (2, 2a) has a moveable stop (4, 4a) which is driven by a position-detection means (6) arranged in the guide. The reversing device is followed by a conveyor belt (27), above which a spray device (28) is arranged so to be displaceable parallel to the test strip. The spray device is equipped with a sensor (45) which stops the conveyor belt (27) when the test strip is located under the spray device.

7 Claims, 3 Drawing Sheets

APPARATUS FOR FEEDING TEST STRIPS AUTOMATICALLY INTO AN ANALYZER

The invention relates to an apparatus for feeding test strips with at least one test zone automatically into an analyzer, the apparatus comprising a part for separating the strips, a part for fixing the position of the test zones and reversing the strips and a part for moistening the test zones of the strip with liquid.

For general urea diagnostics, so-called multiple test strips for determining bilirubin, urobilinogen, ketone bodies, ascorbic acid, glucose, protein, nitrite, pH and blood are available. Test strips of this type contain several test zones, on which the reagents belonging to the particular test are arranged as indicators. The test strips are extracted from a supply container, moistened manually with urine and subsequently introduced into the analyzer. This work is to be automated. An apparatus of the type mentioned in the introduction is to be provided for this purpose.

The invention achieves the object by (a) a supply container for the test strips being provided with an orifice, in which is arranged a transport device equipped with a guide plate and with drivers and having noses which interact with a moveably arranged bar projecting into the orifice in the container, (b) the guide plate merging into a guide which opens into a reversing device for the test strips, there being arranged between the guide and the reversing device a closing means for the guide, the said closing means being connected via a lever to a holding device for the test strips which projects into the guide, is mounted rotatably in synchronism with the closing means and is equipped with a drive device, and the reversing device having a moveable stop which is driven by a position-detection means arranged in the guide and which causes reversal of the test strips, (c) the reversing device being followed by a conveyor belt, above which a spray device for liquid is arranged so as to be displaceable parallel to the test strip, and the spray device being equipped with a sensor which stops the conveyor belt when the test strip is located under the spray device.

The transport device can comprise a roller with drivers on its outer surface, the drivers being designed as noses. On at least one of the end faces of the roller there can be bolts which interact with a pawl, and the pawl can be connected to a return means. Alternatively, the transport device can comprise a conveyor belt which is equipped with drivers and is guided via deflecting rollers and of which the deflecting roller located opposite the orifice has the noses. The reversing device can comprise an evacuable rotatably mounted hollow roller which is arranged at a distance above a transport device for the test strips and which with this forms a gap in which the stop is arranged. The roller can have, on its peripheral surface, a leakage orifice, via which the test strip is sucked up and taken up by the roller when the stop has stopped the test strip. However, the reversing device can also comprise a roller which has a T-shaped slot parallel to its axis of rotation, and the part of the roller located opposite the T-shaped slot is designed as a stop. The spray device can be equipped with at least one sucking-off device for sucking off excess liquid between the individual test zones. However, it can also have a stepping mechanism which stops the spray device above each test zone and which is connected to a valve arranged in the liquid-carrying part of the spray device.

The invention is explained in detail below with reference to the figures which merely illustrate exemplary embodiments. In the drawing.

Figure 1:
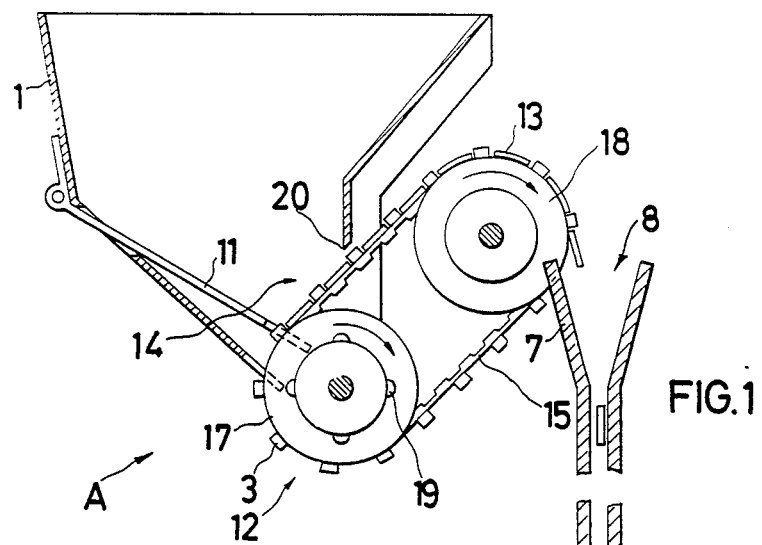
FIG. 1 shows a side view of the apparatus for feeding the test strips.

The apparatus according to the invention comprises a part A for separating the test strips, a part B for fixing the position of the test zones and reversing the test strips and a part C for moistening the test zones with liquid.

Part A comprises a supply container 1 for the test strips 13. The supply container 1 is provided with an orifice 14 which, in practice, is closed by means of the transport device 12. A bar 11 projects into the orifice 14 and is arranged moveably on the supply container or the like. The bar 11 is moved up and down by means of noses 19, 19a, in order to guarantee that the test strips will slip down and prevent bridge formation. The transport device 12 can comprise a conveyor belt 15 which is equipped with drivers 3 and which is guided via deflecting rollers 17, 18. The deflecting roller 17 located opposite the orifice 14 in the supply container 1 is equipped with noses 19 which drive the bar 11. The drivers 3 each pick up a test strip 13 from the supply container and transfer it to a guide plate 7, via which the test strips 13 enter a guide 8. The edge 20 serves as a stripper for excess test strips 13. The transport device 12 can be driven electrically or in another way.

Figure 4:
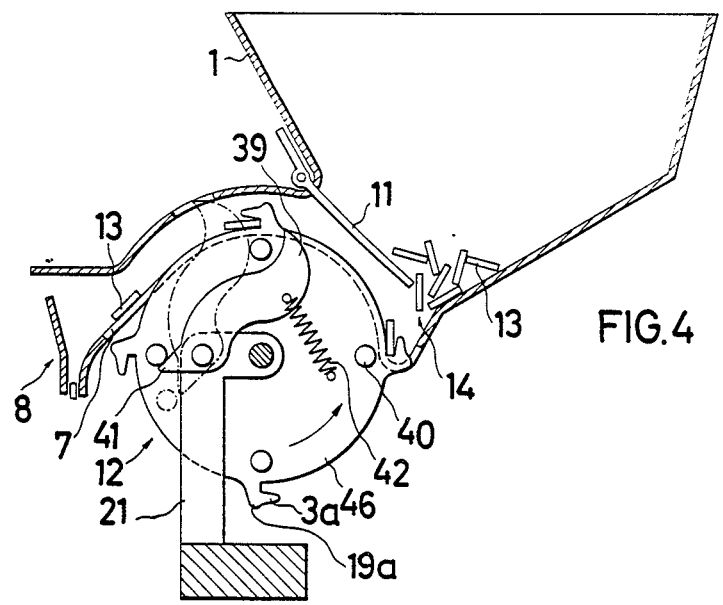
FIG. 4 shows a side view of an alternative form of part A.

The transport device 12 can, however, also comprise a cylindrical roller 46 (FIG. 4), on the outer surface of which are arranged drivers 3a. If claw-shaped drivers are used, it may be expedient to provide a pawl 39, in order to eject the test strips from the driver so that they do not jam between driver 3a and guide plate 7. The pawl 39 is driven by bolts 40 arranged on one end face of the roller 46. It may be expedient to provide pawls and bolts on both end faces. The bolts 40 take up the pawl 39, fastened independently of the roller 46, for example to the bearigg block 21, at the tongue 41.

The return spring 42 brings the pawl into its initial position as soon as it is released by the bolt 40.

Figure 2:
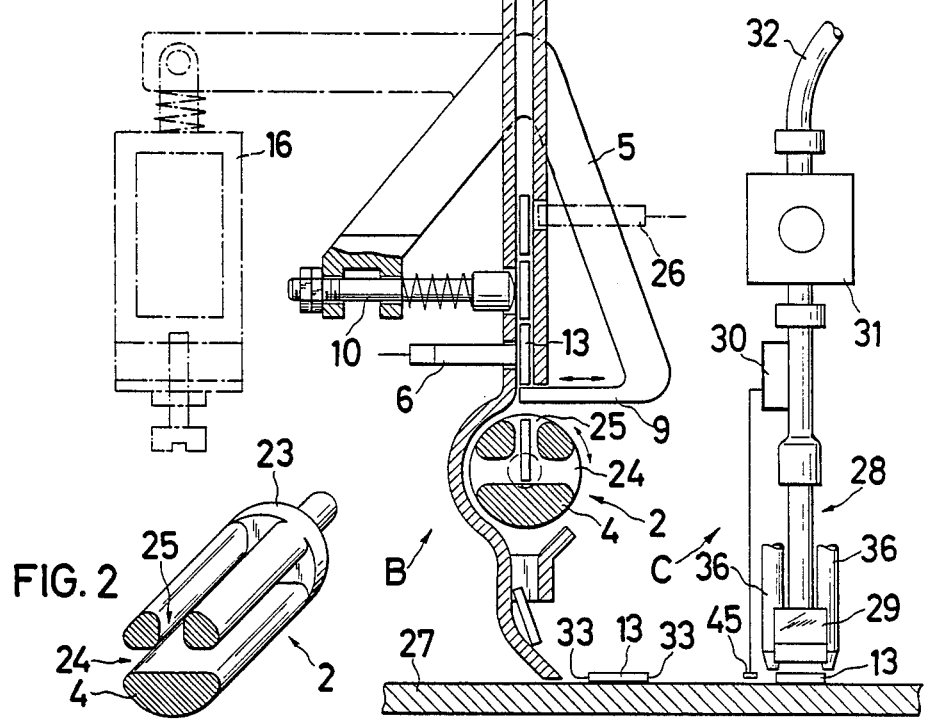
FIG. 2 shows the roller according to FIG. 1 in a perspective representation and partially in section.
Figure 3:
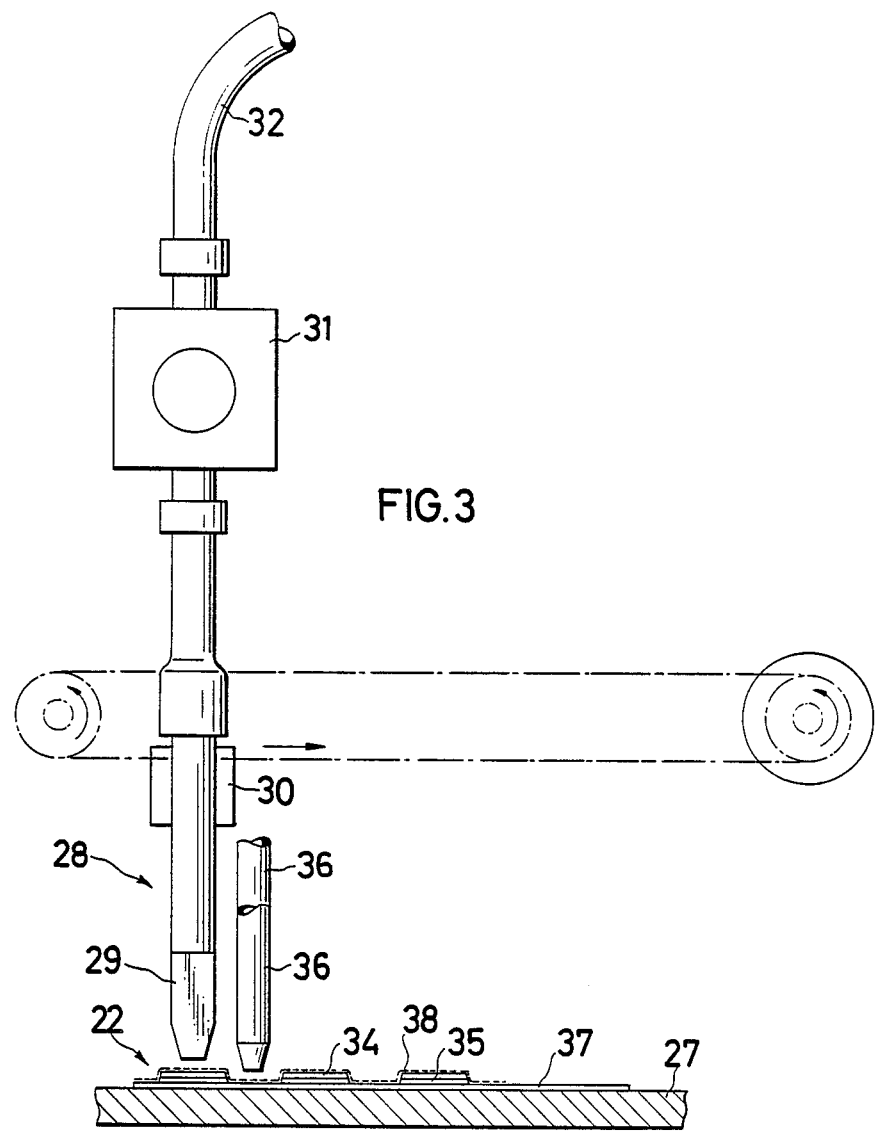
FIG. 3 shows a view of the moistening device.
Figure 5:
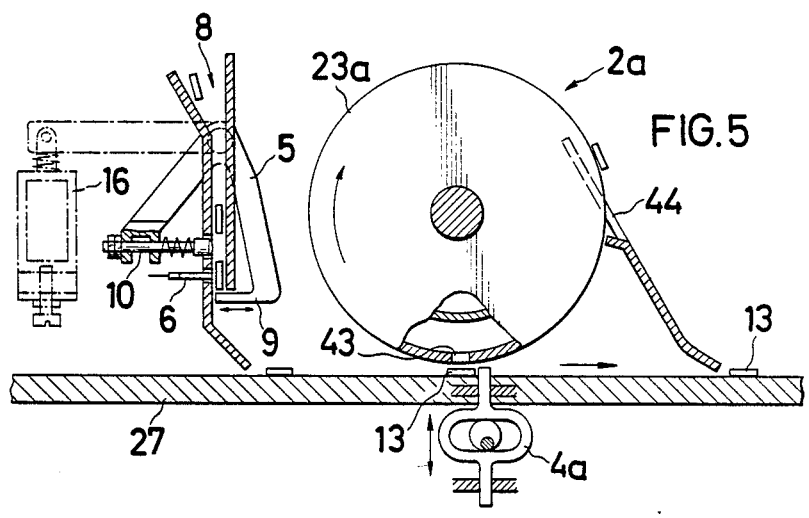
FIG. 5 shows a side view of an alternative form of part B.

Part B has a guide 8 which opens into a reversing device 2, 2a for the test strips 13. Between guide 8 and reversing device 2, 2a is arranged a closing means 9 for the guide. The closing means 9 is connected via a lever 5 to a holding device 10, for example a spring-loaded plunger for the test strips 13. The holding device 10 projects into the guide 8 and is mounted in synchronism with the closing means 9. When the closing means 9 allows the test strip to pass out of the guide 8, the following test strip is retained in the guide by the holding device 10, until the guide is closed again. Holding device and closing means are equipped with a drive device 16. It can be expedient to equip the guide 8 with a monitoring device 26. The reversing device 2, 2a has a stop 4, 4a which is driven by means of the prepared pulses from a position-detection device 6, for example a reflex-light barrier. The position of the test zone 22 on the test strip 13 is determined by means of the position-detection device 6. If the test zone points in the wrong direction, the stop 4, 4a prevents the test strip 13 from being transported further to the part C, namely the moistening device. The test strip 13 is reversed. Reversal can be carried out by means of a roller 23 (FIG. 2) which is equipped, parallel to its axis of rotation, with a slot of T-shaped cross-section. The orifice 24 of the slot is intended as a passage orifice in the roller 23, whilst the slot 25 ends at the stop 4. When the position-detection device 6 signals the correct position of the test strip, test strip can pass through the roller 23 without obstruction. Otherwise, it is stopped by the stop 4 and reversed through 180° as a result of the rotation of the roller 23. However, reversal can also be carried out by means of a hollow roller 23a (FIG. 5) which is evacuable and which has a leakage orifice 43. When the test strip 13 is stopped by the stop 4a, it is sucked up by means of the vacuum through the leakage orifice 43, held on the roller periphery, reversed in the direction of the arrow as a result of the rotation of the roller 23a and taken off the roller by a stripper 44.

In part C, namely the device for moistening the test strips 13, a spray device 28 is arranged above a conveyor belt 27 for the test strips 13. The spray device 28 can be equipped with a wide-slit nozzle 29 and can be shifted parallel to the test strip 13, the nozzle traveling over the individual test zones 22. If the spray device 28 executes a movement in steps, the spray device 28 is equipped with a stepping mechanism 30 which ensures that the nozzle 29 comes to rest above a test zone 22 in each case. A valve 31, which can be arranged in the feed line 32 for the liquid, is actuated at the same time. The valve 31 can be connected mechanically or electrically to the stepping mechanism 30. The slit nozzle 29 is appropriately matched to the geometry of the test zone 22, so that liquid at the sides 33 of the test zones 22 can be absorbed by the absorbent base 35 for the reagent carrier 34. Particularly when the travel over the test zones 22 is continuous, it is necessary to ensure that excess liquid is removed between the individual test zones. The spray device can be equipped with at least one sucking-off device 36 for this purpose. According to FIG. 1, two sucking-off devices 36 are provided. As a rule, the test strip comprises a carrier 37, the test zones 22 and a netting-like cover 38 for protecting the test zones, the lateral regions 33 of the test zones remaining unprotected. The test zones 22 can comprise an absorbent base 35 for the reagent carrier and the reagent carrier 34. The spray device 28 can be equipped with a sensor 45, by means of which the conveyor belt 27 is stopped as soon as a test strip 13 comes to rest underneath the spray device 28. When the transport device 27 is stationary, the separating and reversing devices are likewise stopped.

I claim:

1. An apparatus for feeding test strips with at least one test zone automatically into an analyser, the apparatus comprising a part for separating the test strips, a part for fixing the position of the test zones and reversing the test strips and a part for moistening the test zones of the test strip with liquid, wherein
   (a) a supply container (1) for test strips (13) is provided with an orifice (14), in which is arranged a transport device (12) equipped with a guide plate (7) and with drivers (3) and having noses (19, 19a) which interact with a moveably arranged bar (11) projecting into the orifice in the container (1),
   (b) the guide plate (7) merges into a guide (8) which opens into a reversing device (2, 2a) for the test strips (13), between the guide (8) and the reversing device (2, 2a) is arranged a closing means (9) for the guide (8), the said closing means (9) being connected via a lever (5) to a holding device (10) for the test strips (13) which projects into the guide, is mounted rotatably in synchronism with the closing means (9) and is equipped with a drive device (16), and the reversing device (2, 2a) has a moveable stop (4, 4a) which is driven by means of a position-detection means (6) arranged in the guide (8) and which causes the reversal of the test strips,
   (c) the reversing device (2, 2a) is followed by a conveyor belt (27), above which a spray device (28) for liquid is arranged so as to be displaceable parallel to the test strip, and the spray device is equipped with a sensor (45) which stops the conveyor belt (27) when the test strip (13) is located under the spray device (28).

2. The apparatus as claimed in claim 1, wherein the transport device (12) comprises a roller (46) with drivers (3a) in its outer surface, the drivers (3a) are designed as noses (19a), and on at least one of the end faces of the roller (46) are arranged bolts (40) which interact with a pawl (39) connected to a return means (42).

3. The apparatus as claimed in claim 1, wherein the transport device (12) comprises a conveyor belt (15) which is equipped with drivers (3) and is guided via deflecting rollers (17, 18) and of which the deflecting roller (17) located opposite the orifice (14) has the noses (19).

4. The apparatus as claimed in claim 1, wherein the reversing device (2a) comprises an evacuable rotatably mounted hollow roller (23a) which is arranged at a distance above a conveyor belt (27) for the test strips (13) and which with this forms a gap in which the stop (4a) is arranged, and the roller has, on its peripheral surface, a leakage orifice (43), via which the test strip is sucked up and taken up by the roller when the stop (4a) has stopped the test strip.

5. The apparatus as claimed in claim 1, wherein the reversing device (2) comprises a roller (23) which has a T-shaped slot parallel to its axis of rotation, and the part of the roller (23) located opposite the T-shaped slot (25) is designed as a stop (4).

6. The apparatus as claimed in claim 1, wherein the spray device (28) is equipped with at least one sucking-off device (36) for sucking off excess liquid between the individual test zones (22).

7. The apparatus as claimed in claim 1, wherein the spray device (28) is equipped with a stepping mechanism (30) which stops the spray device above each test zone (22) and which is connected to a valve (31) arranged in the liquid-carrying part of the spray device (28).

* * * * *